(12) United States Patent
Kohn et al.

(10) Patent No.: US 6,319,492 B1
(45) Date of Patent: *Nov. 20, 2001

(54) COPOLYMERS OF TYROSINE-BASED POLYARYLATES AND POLY(ALKYLENE OXIDES)

(75) Inventors: Joachim B. Kohn, Highland Park; Chun Yu, Piscataway, both of NJ (US)

(73) Assignee: Rutgers, The State University, New Brunswick, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/520,665

(22) Filed: Mar. 7, 2000

Related U.S. Application Data

(62) Division of application No. 09/085,571, filed on May 27, 1998, now Pat. No. 6,048,521.

(51) Int. Cl.$^7$ ........................................................ A61K 31/74
(52) U.S. Cl. .......................... 424/78.08; 424/422; 424/423; 424/426; 525/432; 528/176
(58) Field of Search ............................ 525/432; 528/176; 424/78.08, 422, 423, 426

(56) References Cited

U.S. PATENT DOCUMENTS

| | | | |
|---|---|---|---|
| 4,857,602 | * | 8/1989 | Casey et al. ............................ 525/408 |
| 5,658,995 | * | 8/1997 | Kohn et al. ............................ 525/432 |
| 5,670,602 | * | 9/1997 | Kohn et al. ............................ 528/176 |

* cited by examiner

Primary Examiner—Thurman K. Page
Assistant Examiner—Liliana Di Nola-Baron
(74) Attorney, Agent, or Firm—Synnestvedt & Lechner LLP

(57) ABSTRACT

Implantable medical devices and drug delivery implants containing polyarylate random block copolymers are disclosed, along with methods for drug delivery and for preventing the formation of adhesions between injured tissues employing the polyarylate random block copolymers.

4 Claims, 3 Drawing Sheets

COPOLYMERS OF TYROSINE-BASED POLYARYLATES AND POLY(ALKYLENE OXIDES)

CROSS REFERENCE TO RELATED APPLICATIONS

The present application is a divisional of U.S. patent application Ser. No. 09/085,571 filed May 27, 1998, now U.S. Pat. No. 6,048,521 the disclosure of which is incorporated herein by reference, which application in turn, claims the priority benefit under 35 U.S.C. §120 of the Nov. 27, 1996 International filing date of co-pending PCT Application No. PCT/US 96/19098, designating the United States, which in turn claims the priority benefit under 35 U.S.C. §120 from the Nov. 27, 1995 filing date of U.S. patent application Ser. No. 08/562,842, now U.S. Pat. No. 5,658,995. The disclosures of the PCT Application and U.S. Pat. No. 5,658,995 are incorporated herein by reference. The present application also claims priority benefit of U.S. Provisional Application Ser. No. 60/064,905 filed Nov. 7, 1997 and No. 60/081,502 filed Apr. 13, 1998, the disclosures of both of which are also incorporated herein by reference thereto. This application also claims priority benefit of U.S. patent application Ser. No. 09/056,050 filed Apr. 7, 1998, now U.S. at. No. 6,120,437 which, in turn, claims the priority benefit of U.S. Provisional Patent Ser. No. 60/064,656 filed on Nov. 7, 1997. The disclosures of both the aforementioned standard U.S. patent application and the U.S. provisional patent application from which it claims priority benefit are also incorporated herein by reference.

BACKGROUND OF THE INVENTION

The present invention relates to copolymers of tyrosine-based polycarbonates and poly(alkylene oxide) and to methods of synthesizing such polymers.

Linear aromatic polycarbonates derived from diphenols such as bisphenol-A represent an important class of condensation polymers. Such polycarbonates are strong, tough, high melting materials. They are well-known in the literature and are commercially produced in large quantities.

The early investigations on block copolymers of poly(bisphenol-A carbonate) and poly(alkylene oxide) started in 1961 and were conducted by the groups of Merrill and Goldberg. Merrill, *J. Polym. Sci.*, 55 343–52 (1961) for the first time introduced poly(alkylene oxide) blocks into poly(bisphenol-A carbonate). Merrill described the interfacial copolymerization of poly(bisphenol-A carbonate) (dissolved in methylene chloride) and poly(alkylene oxide) bischloroformate (dissolved in aqueous sodium hydroxide). The presence of flexible blocks of poly(alkylene oxide) promoted the crystallization of the polycarbonate, which resulted in flexible polymers with high melting points. Later on, Goldberg, *J. Polym. Sci., Part C*, 4, 707–30 (1964) reported more work on block copolymers of poly(bisphenol-A carbonate) and poly(ethylene oxide). The incorporation of flexible, polar, water soluble block segments into the rigid, linear, aromatic polycarbonate chains produced elastomers with unusual thermal and plastic properties. In particular Goldberg described the use of poly(ethylene oxide) as a comonomer with bisphenol-A. The synthesis was based on the reaction of phosgene with the mixture of monomers in pyridine followed by purification of the copolymer by precipitation in isopropanol. Copolymers were studied for structure-property correlations as a function of poly(ethylene oxide) molecular weight and copolymer composition. Remarkable strength and snappy elasticity were observed at poly(ethylene oxide) block concentration greater than 3 mole-%. These thermoplastic elastomers also exhibited high softening temperatures (>180° C.) and tensile elongations up to about 700%. Both glass transition temperature and softening temperature varied linearly with the molar ratio of poly(ethylene oxide). The early studies established that these copolymers are good elastomers, but no medical applications were considered.

Later on, Tanisugi et al., *Polym. J.*, 17(3), 499–508 (1985); Tanisugi et al., *Polym. J.*, 16(8), 633–40 (1984); Tanisugi et al., *Polym. J.*, 17(8), 909–18(1984); Suzuki et al., *Polym. J.*, 16(2), 129–38 (1983); and Suzuki et al., *Polym. J.*, 15(1), 15–23 (1982) reported detailed studies of mechanical relaxation, morphology, water sorption, swelling, and the diffusion of water and ethanol vapors through membranes made from the copolymers.

Mandenius et al., *Biomaterials*, 12(4), 369–73 (1991) reported plasma protein absorption of the copolymer, compared to polysulphone, polyamide and polyacrylonitrile as membranes for blood purification. Adhesion of platelets onto Langmuir and solvent cast films of the copolymers was also reported by Cho et al., *J. Biomed. Mat Res.*, 27, 199–206 (1993). The use of copolymers of poly(bisphenol-A carbonate) and poly(alkylene oxide) as hemodialysis membrane or plasma separator was disclosed in U.S. Pat. Nos. 4,308,145 and 5,084,173 and in EP 46,817; DE 2,713,283; DE 2,932,737 and DE 2,932,761.

Heretofore, block copolymers of polycarbonates and poly(alkylene oxide) have not been studied as medical implantation materials. Although an extensive search of the literature revealed no studies of in vitro or in vivo degradation, one of ordinary skill in the art would not expect that the currently known block copolymers of poly(bisphenol-A carbonate) and poly(alkylene oxide) would degrade under physiological conditions at rates suitable for the formulation of degradable implants.

U.S. Pat. Nos. 5,198,507 and 5,216,115 disclosed tyrosine-derived diphenolic monomers, the chemical structure of which was designed to be particularly useful in the polymerization of polycarbonates, polyiminocarbonates and polyarylates. The resulting polymers are useful as degradable polymers in general, and as tissue compatible bioerodible materials for biomedical uses in particular. The suitability of these polymers for this end-use application is the result of their derivation from naturally occurring metabolites, in particular, the amino acid L-tyrosine.

Tyrosine-based polycarbonates are strong, tough, hydrophobic materials that degrade slowly under physiological conditions. For many medical applications such as drug delivery, non-thrombogenic coatings, vascular grafts, wound treatment, artificial skin, relatively soft materials are needed that are more hydrophilic and degrade faster than the available tyrosine-based polycarbonates.

SUMMARY OF THE INVENTION

In this invention, the introduction of poly(alkylene oxide) segments into the backbone of tyrosine-based polycarbonates was found to lead to softer, more hydrophilic polymers that exhibited significantly increased rates of degradation. Since the previously known block copolymers of poly(bisphenol-A carbonate) and poly(alkylene oxide) apparently do not degrade appreciably under physiological conditions, the finding was unexpected that the incorporation of poly(alkylene oxide) into tyrosine-based polycarbonate significantly increased the rate of degradation. Furthermore, the disclosed copolymers of tyrosine-based polycarbonate and poly(ethylene oxide) have an alkyl ester pendent chain at each monomeric repeat unit. This pendent chain is an unprecedented structural feature among the currently known block copolymers of poly(bisphenol A carbonate) and poly(alkylene oxide). As shown in more detail below, variation in the length of the pendent chain can be used to fine-tune the polymer properties. Studies of this kind are known in the literature for other polymer systems, but have not been performed for block copolymers of poly(bisphenol A carbonate) and poly(alkylene oxide). In addition, the presence of a carboxylic acid containing pendent chain can facilitate the attachment of biologically or pharmaceutically active moieties to the polymer backbone. This, too, is an unprecedented feature among the previously known copolymers of bisphenol-A and poly(alkylene oxide).

Therefore, according to one aspect of the present invention, a random block copolymer of a tyrosine-derived diphenol monomer and a poly(alkylene oxide) is provided having the structure of Formula I:

For nonionic synthetic polymers such as protein-based bioelastic materials, poly(N-isopropylacrylamide) and poly (ethylene glycol)-poly(propylene glycol) copolymers, as well as the copolymers of the present invention, the driving force of phase transition is the combination of hydrogen bonding and hydrophobic effect. As the temperature increases, the gels of these polymers undergo a phase transition from a swollen to a collapsed state, while polymer solutions precipitate at certain temperature or within certain temperature ranges. These polymers, including the copolymers of the present invention, and especially those that undergo a phase transition at about 30–40° C. on heating can be used as biomaterials for drug release and clinical implantation materials. Specific applications include the prevention of adhesions and tissue reconstruction.

Therefore, the present invention also includes implantable medical devices containing the random block copolymers of the present invention. In one embodiment of the present invention, the copolymers are combined with a quantity of a biologically or pharmaceutically active compound sufficient for therapeutically effective site-specific or systemic

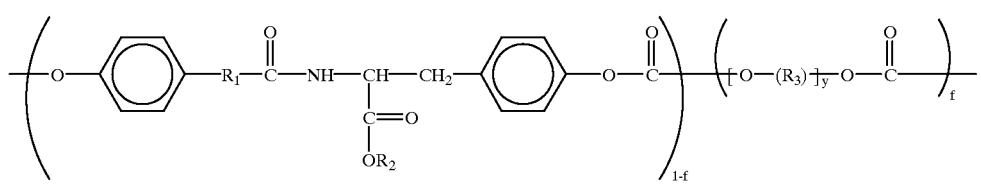

wherein

R$_1$ is —CH=CH— or (—CH$_2$—)$_j$, in which j is zero or an integer from one to eight;

R$_2$ is selected from straight and branched alkyl and alkylaryl groups containing up to 18 carbon atoms and optionally containing at least one ether linkage and derivatives of biologically and pharmaceutically active compounds covalently bonded to the copolymer;

each R$_3$ is independently selected from alkylene groups containing from 1 up to 4 carbon atoms;

y is between about 5 and about 3000; and f is the percent molar fraction of alkylene oxide in the copolymer, and ranges between about 1 and about 99 mole percent.

Another important phenomena that was observed for the copolymers is the temperature dependent inverse phase transition of the polymer gel or the polymer solution in aqueous solvents. Inverse temperature transitions have been observed for several natural and synthetic polymer systems such as proteins and protein-based polymers as described by Urry, *Tissue Engineering: Current Perspectives* (Boston Birkhauser, New York), 199–206, poly(acrylic acid) derived copolymers as described by Annaka et al., *Nature*, 355, 430–32(1992); Tanaka et al., *Phys. Rev. Lett.*, 45(20), 1636–39(1980) and Hirokawa et al., *J. Chem. Phys.*, 81(12), 6379–80(1984), and poly(ethylene glycol)-poly(propylene glycol) copolymers as described by Armstrong et al., *Macromol. Reports*, A31(suppl. 6&7), 1299–306(1994). Polymer gels and solutions of these polymers are known to undergo continuous or discontinuous volume change upon changes in temperature, solvent composition, pH or ionic composition. The driving forces for the phase change can be attractive or repulsive electrostatic interactions, hydrogen bonding or hydrophobic effects.

drug delivery as described by Gutowska et al., *J. Biomater. Res.*, 29, 811–21 (1995) and Hoffman, *J. Controlled Release*, 6, 297–305 (1987). In another embodiment of the present invention, the copolymer is in the form of a sheet or a coating applied to exposed injured tissue for use as a barrier for the prevention of surgical adhesions as described by Urry et al., *Mat. Res. Soc. Symp. Proc.*, 292, 253–64 (1993).

Furthermore, another aspect of the present invention provides a method for site-specific or systemic drug delivery by implanting in the body of a patient in need thereof an implantable drug delivery device containing a therapeutically effective amount of a biologically or physiologically active compound in combination with the random block copolymer of the present invention. Yet another aspect of the present invention provides a method for preventing the formation of adhesions between injured tissues by inserting as a barrier between the injured tissues a sheet or a coating of the random block copolymer of the present invention.

As noted above, the tyrosine-derived diphenol monomers are also useful in the polymerization of polyarylates. The introduction of poly(alkylene oxide) segments into the backbone of tyrosine-based polyarylates would also be expected to lead to softer, more hydrophilic polymers with significantly increased rates of degradation. Therefore, according to still yet another aspect of the present invention, aliphatic and aromatic polyarylates are provided, polymerized as random block copolymers of a dicarboxylic acid with a tyrosine-derived diphenol and a poly(alkylene oxide), wherein an equimolar combined quantity of the diphenol and the poly(alkylene oxide) is reacted with a dicarboxylic acid in a molar ratio of the diphenol to the poly(alkylene oxide) between about 1:99 and about 99:1;

wherein the tyrosine-derived diphenol has the structure of Formula II:

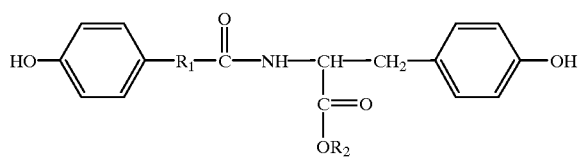

(II)

in which $R_1$ and $R_2$ are the same as described above with respect to Formula I;

the dicarboxylic acid has the structure of Formula III:

(III)

in which R is selected from saturated and unsaturated, substituted and unsubstituted alkyl, aryl and alkylaryl groups containing up to 18 carbon atoms; and the poly(alkylene oxide) has the structure of Formula IV:

(IV)

in which each $R_3$ is independently selected from alkylene groups containing up to 4 carbon atoms and y is between about 5 and about 3000.

The random block copolymers of the present invention suitable for use as implantable medical devices, or in methods for site-specific or systemic drug delivery, or in methods for preventing the formation of adhesions between injured tissues include the polyarylates of the present invention.

Copolymers based on tyrosine-derived diphenols and poly(alkylene oxide) represent a new group of nonionic polymers that show inverse temperature transitions. These copolymers contain natural amino acids as building blocks, are degradable under physiological conditions, and have been shown to be biocompatible. By changing the tyrosine-derived diphenol, the poly(alkylene oxide) and the ratio of the two components, the copolymers can be designed and synthesized to exhibit desired transition temperatures.

DETAILED DESCRIPTION OF THE PREFERRED EMBODIMENT

Figure 1:
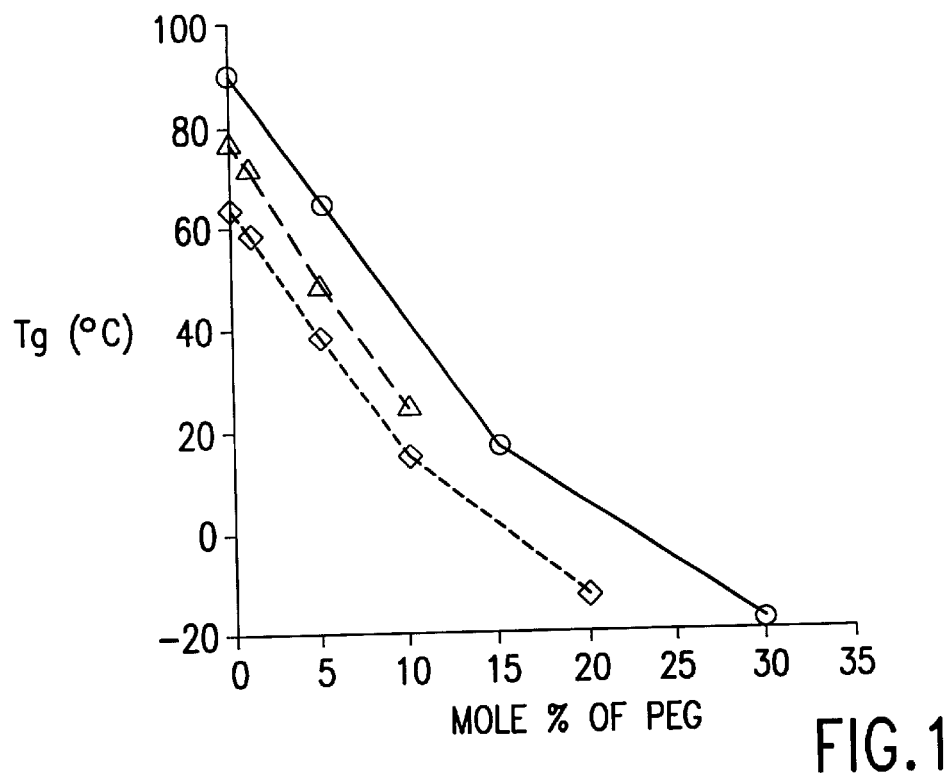
FIG. 1 depicts the glass transition temperatures of poly(DTE co $PEG_{1,000}$ carbonates) (○), poly(DTB co $PEG_{1,000}$ carbonates) (△) and poly(DTH co $PEG_{1,000}$ carbonates) (◇) of the present invention having different PEG contents and in comparison to corresponding polycarbonate homopolymers.

The above-defined polymers of Formula I are random block copolymers of the above-defined tyrosine-derived diphenols of Formula II with the above-defined poly(alkylene oxide) of Formula IV. The defined units of tyrosine derived diphenols and poly(alkylene oxide) do not imply the presence of defined blocks within the structure of Formula I. The percent molar fraction of alkylene oxide, f, in the copolymer may range between about 1 and about 99 mole percent, with a molar fraction of alkylene oxide between about 5 and about 95 mole percent being preferred. The mole percent of alkylene oxide may vary over the entire range, with polymers having levels of alkylene oxide higher than 5 mole percent being resistant to cell attachment. Polymers with levels higher than 70 mole percent are water soluble. Polymers with any level of alkylene oxide are useful, in drug delivery, with water-soluble compositions being preferred for drug-targeting applications.

The diphenols shown in Formula II are described in co-pending and commonly owned U.S. patent application Ser. No. 08/414,339 filed Mar. 31, 1995. The disclosure of this patent is incorporated herein by reference.

In Formula II, and thus consequently in Formula I, $R_1$ is preferably —$CH_2$—$CH_2$— and $R_2$ is preferably a straight chain ethyl, butyl, hexyl or octyl group. $R_2$ may contain at least one ether linkage. When $R_1$ is —$CH_2$—$CH_2$—, the diphenol compound of Formula I is referred to as a desaminotyrosyl-tyrosine alkyl ester. The most preferred member of the group of desaminotyrosyl-tyrosine alkyl esters is the hexyl ester, referred to as desaminotyrosyl-tyrosine hexyl ester or DTH.

The diphenol compounds may be prepared as described in the above-referenced U.S. patent application Ser. No. 08/414,339. The method described in U.S. Pat. No. 5,099,060 may also be employed, and is incorporated herein by reference.

The poly(alkylene oxide) shown in Formula IV can be any commonly used alkylene oxide known in the art, as is preferably a poly(ethylene oxide), poly(propylene oxide) or poly(tetra methylene oxide). Poly(alkylene oxide) blocks containing ethylene oxide, propylene oxide or tetramethylene oxide units in various combinations are also possible constituents within the context of the current invention.

The poly(alkylene oxide) is most preferably a poly(ethylene oxide) in which y of Formula IV is between about 20 and about 200. More preferred embodiments are obtained when poly(ethylene oxide) blocks with a molecular weight of about 1,000 to about 20,000 g/mol are used. For these preferred embodiments, in the structure of Formula IV, both $R_3$ groups are hydrogen and y has values from about 22 to about 220. A value for y ranging between about 22 and about 182 is even more preferred.

The random block copolymers of Formula I may be prepared by the conventional methods for polymerizing diphenols into polycarbonates described in the aforementioned U.S. Pat. No. 5,099,060, which methods are also incorporated herein by reference. This involves the reaction of the desired ratio of tyrosine-derived diphenol and poly (alkylene oxide) with phosgene or phosgene precursors (e.g., diphosgene or triphosgene) in the presence of a catalyst. Thus, the copolymers of Formula I may be prepared by interfacial polycondensation, polycondensation in a homogeneous phase or by transesterification. The suitable processes, associated catalysts and solvents are known in the art and are taught in Schnell, *Chemistry and Physics of Polycarbonates*, (Interscience, New York 1964), the teachings of which are also incorporated herein by reference. One of ordinary skill in the art will be able to extend the disclosed techniques to the random block copolymerization of a tyrosine-derived diphenol with a poly(allylene oxide) without undue experimentation.

The random block copolymers of Formula I have weight-average molecular weights above about 20,000 daltons, and preferably above about 30,000 daltons. The number-average molecular weights of the random block copolymers of Formula I are above about 10,000 daltons, and preferably above about 20,000 daltons. Molecular weight determinations are calculated from gel permeation chromatography relative to polystyrene standards without further correction.

As disclosed above, $R_2$ of the random block copolymer of Formula I and the tyrosine-derived diphenol of Formula II can be a derivative of a biologically or pharmaceutically active compound covalently bonded to the copolymer or diphenol. $R_2$ is covalently bonded to the copolymer or diphenol by means of an amide bond when in the underivatized biologically or pharmaceutically active compound a primary or secondary amine is present at the position of the amide bond in the derivative. $R_2$ is covalently bonded to the copolymer or diphenol by means of an ester bond when in the underivatized biologically or pharmaceutically active compound a primary hydroxyl is present at the position of the ester bond in the derivative. The biologically or pharmaceutically active compound may also be derivatized at a ketone, aldehyde or carboxylic acid group with a linkage moiety that is covalently bonded to the copolymer or diphenol by means of an amide or ester bond.

Examples of biologically or pharmaceutically active compounds suitable for use with the present invention include acyclovir, cephradine, malphalen, procaine, ephedrine, adriamycin, daunomycin, plumbagin, atropine, quinine, digoxin, quinidine, biologically active peptides, chlorin $e_6$, cephradine, cephalothin, melphalan, penicillin V, aspirin, nicotinic acid, chemodeoxycholic acid, chlorambucil, and the like. The compounds are covalently bonded to the copolymer or diphenol by methods well understood by those of ordinary skill in the art. Drug delivery compounds may also be formed by physically blending the biologically or pharmaceutically active compound to be delivered with the random block copolymers of the present invention using conventional techniques well-known to those of ordinary skill in the art.

The tyrosine-derived diphenol compounds of Formula II and the poly(alkylene oxide) of Formula IV may also be reacted according to the method disclosed by U.S. Pat. No. 5,216,115 to form polyarylates, the disclosure of which is hereby incorporated by reference thereto. As disclosed by U.S. Pat. No. 5,216,115, the diphenol compounds are reacted with the aliphatic or aromatic dicarboxylic acids of Formula III in a carbodiimide mediated direct polyesterification using 4-(dimethylamino)pyridinium-p-toluene sulfonate (DPTS) as a catalyst to form aliphatic or aromatic polyarylates. Random block copolymers with poly(alkylene oxide) may be formed by substituting poly(alkylene oxide) for the tyrosine derived diphenol compound in an amount effective to provide the desired ratio of diphenol to poly (alkylene oxide) in the random block copolymer.

The random block copolymers of the present invention, both polycarbonate and polyarylates, can be worked up by known methods commonly employed in the field of synthetic polymers to produce a variety of useful articles with valuable physical and chemical properties, all derived from tissue-compatible monomers. The useful articles can be shaped by conventional polymer-forming techniques such as extrusion, compression molding, injection molding, solvent casting, spin casting, and the like. Shaped articles prepared from the polymers are useful, inter alia, as degradable biomaterials for medical implant applications. Such applications include the use of the shaped articles as vascular grafts and stents, bone plates, sutures, implantable sensors, barriers for surgical adhesion prevention, implantable drug delivery devices, scaffolds for tissue regeneration, and other therapeutic aids and articles which decompose harmlessly within a known period of time. The polymers can also be formed as a coating on the surface of implants by conventional dipping or spray coating techniques to prevent the formation of adhesions on the implant.

Implantable articles formed from the random block copolymers of the present invention must be sterile. Sterility is readily accomplished by conventional methods such as irradiation or treatment with gases or heat.

The following non-limiting examples set forth hereinbelow illustrate certain aspects of the invention. All parts and percentages are by weight unless otherwise noted and all temperatures are in degrees Celsius.

Materials and Methods

Materials

L-Tyrosine, thionyl chloride, pyridine, methylene chloride, tetrahydrofuran (THF), ethanol, butanol, hexanol, octanol, 3-(4-hydroxy-phenyl)propionic acid (desaminotyrosine, Dat), dicyclohexyl carbodiimide (DCC), and hydroxybenzotriazole (HOBt) were obtained from Aldrich, phosgene (solution in toluene) was obtained from Fluka. All solvents were of HPLC grade and were used as received.

Spin Casting

The bottom glass slide of dual chamber units (#177380, Nunc, Inc.) was spin cast first with a styrene silane copolymer solution (2.5% w/v in ethyl acetate), as described by Ertel et al., *J. Biomat. Sci. Polym. Edn.* 3, 163–83 (1991), which served as a coupling agent, and then with the polymer solution (2% w/v in methylene chloride) for 30 s at 800 rpm. The coated slides were dried under vacuum for one week prior to cell culture. Poly(bisphenol-A carbonate) was similarly spin cast and included as a control in the cell growth studies.

Compression Molding

Thin polymer films were prepared by compression molding. Processing temperature was 30–35° C. above Tg for each polymer. To minimize polymer adhesion to the metal plates of the mold, two teflon sheets were added between the polymer and metal plates of the mold.

Spectroscopy

FT-IR spectra were recorded on a Matson Cygnus 100 spectrometer. Polymer samples were dissolved in methylene chloride and films were cast directly onto NaCl plates. All spectra were collected after 16 scans at 2 cm$^{-1}$ resolution. UV/Vis spectra were recorded on a Perkin-Elmer Lambda 3B spectrophotometer. NMR spectra of polymer solutions in deuterated chloroform were recorded on a Varian VXR-200 spectrometer (64 scans).

Gel Permeation Chromatography (GPC)

The chromatographic system consisted of a Perkin-Elmer Model 410 pump, a Waters Model 410 RI detector, and a PE-Nelson Model 2600 computerized data station. Two PL-gel GPC columns (pore size $10^5$ and $10^3$ Å) were operated in series at a flow rate of 1 ml/min using THF. Molecular weights were calculated relative to polystyrene standards without further correction.

Thermal Analysis

The glass transition temperature ($T_g$) was determined by differential scanning calorimetry (DSC) on a DuPont 910 DSC instrument calibrated with indium. Each specimen was subjected to two consecutive DSC scans. After the first run the specimen was quenched with liquid nitrogen and the second scan was performed immediately thereafter. $T_g$ was determined in the second DSC scan as the midpoint. The heating rate for all polymers was 10° C./min and the average sample size was 10 mg.

Water Uptake

A piece of copolymer (15–20 mg) was cut from a film incubated in PBS at 37° C., and wiped to remove water on the surface of the sample. Water content (WC in %) was determined by thermogravimetric analysis (TGA) on a DuPont 951 TGA instrument at a heating rate of 10° C./min and was reported as percentage weight lost below 200° C. Water uptake was calculated as WC/(1-WC).

Hydrolytic Degradation Studies

Samples were cut from compression molded films and incubated at 37° C. in phosphate buffer saline (0.1 M, pH 7.4) (PBS) containing 200 mg/L of sodium azide to inhibit bacterial growth. The degradation process was followed by recording weekly the changes in the molecular weight of the polymer. Results are the average of two separate specimens per polymer.

Microsphere Processing

Microspheres were prepared by solvent evaporation as described by Mathiowitz et al., *J. App. Polym. Sci.*, 35, 755–74 (1988). 0.05 g of copolymer was dissolved in 1 mL of methylene chloride. The polymer solution was injected into 50 mL of an aqueous solution of poly(vinyl alcohol) (PVA) in a 150 mL beaker with 3 baffles. The mixture was stirred by a overhead stirrer with a propeller at 1300 rpm. After 4 h of stirring, the microspheres were collected by membrane filtration and washed 6 times with water to remove as much PVA as possible. Then the microspheres were dried to constant weight under high vacuum.

Drug Loading and Release p-Nitroaniline (pNA) was dissolved in the polymer solution followed by microsphere formation as described above. pNA loading was determined by UV spectroscopy ($\lambda$=380 nm) after complete dissolution of an exactly weighed amount of microspheres in methylene chloride.

FITC-dextrans were dissolved in 50 ml of water and dispersed in the polymer solution by sonication (w/o/w method) followed by microsphere formation as described above. To determine the FITC-dextran loading, the microspheres were dissolved in methylene chloride and the FITC-dextran was extracted into aqueous phosphate buffer solution (0.1 M, pH 7.4) followed by florescence spectrophotometry (excitation: 495 nm, emission: 520 nm).

An exactly weighed amount of pNA or FITC-dextran loaded microspheres were placed in an exactly measured volume of phosphate buffer solution (0.1 M, pH 7.4) at 37° C. in a water shaker bath. The amount of pNA or FITC-dextran released into the buffer solution was determined as described above.

Cell Growth

Fetal rat lung fibroblasts (#CCL192, American Tissue Culture Collection) were grown in Ryan Red medium with 50 mg/ml sodium ascorbate and 10% fetal calf serum as described by Poiani et al., *Amino Acids*, 4, 237–48 (1993) and Ryan et al., *J. Tiss. Cult. Meth.*, 10, 3–5 (1986). For polymer evaluation, the dual chamber units (#177380, Nunc, Inc.) were spin cast first with a styrene silane copolymer solution (2.5% w/v in ethyl acetate), which served as a coupling agent, and then with the polymer solution of interest. Unmodified plastic (#177429, Nunc) and glass dual chamber units (#177380, Nunc) served as controls and were used as received. Prior to cell seeding, all surfaces were incubated for 3 hours with PBS containing 5% penicillin-streptomycin. Cells from passage 5 were subsequently seeded at a density of $10^4$ cells/cm$^2$. After 1 or 5 days of incubation, the cells were gently rinsed with PBS, and trypsinized from 3 separate chambers. The suspension was counted 4 times in a hemocytometer.

Measurement of Inverse Temperature Transition

The detection of inverse phase transition is based on the increase in turbidity as the initial soluble polymerprecipitates upon heating. The increase in turbidity is monitored by visible spectroscopy as described below.

Polymer solutions: Optical Density (OD) measurements for 0.05% (w/v) polymer aqueous solutions were performed at 500 nm on a diode array spectrophotomer (Hewlett Packard, Model 8452-A) with a water-jacketed cell holder coupled with a refrigerated circulating bath (Neslab, model RTE-8). Temperature was manually controlled at rates of 0.5° C./min. and monitored by a microprocessor thermometer (Omega, model HH22). The initial breaking point in the resulting optical density versus temperature curve was taken as the onset of the temperature of transition.

Nomenclature

Copolymer structure and composition is represented in the following way: in poly(DTX co fPEG$_{Mw}$ carbonate), X relates to the length of the alkyl ester pendent chain. In the examples described below E (ethyl), B (butyl), and H (hexyl) were used. The percent molar fraction of poly (ethylene oxide) content in the copolymer is represented by the letter f. In the samples listed below, the value of f was varied from 1 to 70 mole %. $M_w$ represents the average molecular weight of the PEG blocks used in the synthesis of the copolymer. Thus, Poly (DTE co 5% PEG1,000 carbonate) refers to a copolymer prepared from the ethyl ester of desaminotyrosyl-tyrosine, and 5 mole % of PEG blocks having an average molecular weight of 1000 g/mol.

EXAMPLES

Example 1

Poly(DTE co 5% PEG$_{1,000}$ carbonate) was synthesized as follows:

10.85 g of DTE (30.4 mmole) and 1.57 g of PEG$_{1,000}$ (1.59 mmole) were placed into a 250 ml flask. Then 60 ml of dry methylene chloride and 9.6 ml of anhydrous pyridine were added. At room temperature, 20.6 ml of a 1.93 M solution of phosgene in toluene was added slowly to the solution with overhead stirring during 90 minutes. 180 ml THF was added to dilute the reaction mixture. The copolymer was precipitated by slowly adding the mixture into 2400 ml of ethyl ether. The copolymer was redissolved in 220 ml THF (5% w/v solution) and reprecipitated by slowly adding the polymer solution into 2200 ml of water.

10.8 g of a white copolymer was obtained. As determined by GPC using THF as the solvent, the copolymer has a weight average molecular weight of 127,000 daltons, a number average molecular weight of 84,000 daltons and a polydispersity of 1.5.

Example 2

Poly(DTE co 30% $PEG_{1,000}$ carbonate) was synthesized as follows:

5.23 g of DTE (14.6 mmole) and 6.20 g of $PEG_{1,000}$ (6.27 mmole) were placed into a 250 ml flask. Then 60 ml of dry methylene chloride and 6.7 ml of anhydrous pyridine were added. At room temperature, 13.5 ml of a 1.93 M solution of phosgene in toluene was added slowly to the solution with overhead stirring during 90 minutes. 180 ml THF was added to dilute the reaction mixture. The copolymer was precipitated by slowly adding the mixture into 2400 ml of ethyl ether. The copolymer was redissolved in 200 ml THF (5% w/v solution) and reprecipitated by slowly adding the polymer solution into 2000 ml of water.

8.9 g of a white copolymer was obtained. As determined by GPC using THF as the solvent, the copolymer has a weight average molecular weight of 41,000 daltons, a number average molecular weight of 31,000 daltons and a polydispersity of 1.3.

Example 3

Poly(DTO co 5% $PEG_{1,000}$ carbonate) was synthesized as follows:

9.23 g of DTO (20.9 mmole) and 1.09 g of $PEG_{1,000}$ (1.1 mmole) were placed into a 250 ml flask. Then 50 ml of dry methylene chloride and 7.0 ml of anhydrous pyridine were added. At room temperature, 14.3 ml of a 1.93 M solution of phosgene in toluene was added slowly to the solution with overhead stirring during 90 minutes. 150 ml THF was added to dilute the reaction mixture. The copolymer was precipitated by slowly adding the mixture into 2000 ml of ethyl ether. The copolymer was redissolved in 200 ml THF (5% w/v solution) and reprecipitated by slowly adding the polymer solution into 2000 ml of water.

9.1 g of a white copolymer was obtained. As determined by GPC using THF as the solvent, the copolymer has a weight average molecular weight of 32,000 daltons, a number average molecular weight of 13,000 daltons and a polydispersity of 2.5.

Example 4

Poly(DTE co 0.262% $PEG_{20,000}$ carbonate) was synthesized as follows:

10.24 g of DTE (28.6 mmole) and 1.5 g of $PEG_{20,000}$ (0.075 mmole) were placed into a 250 ml flask. Then 60 ml of dry methylene chloride and 8.7 ml of anhydrous pyridine were added. At room temperature 18.6 ml of 1.93 M solution of phosgene in toluene was added slowly to the solution with overhead stirring during 90 minutes. 180 ml THF was added to dilute the reaction mixture. The copolymer was precipitated by slowly adding the mixture into 2400 ml of ethyl ether. The copolymer was redissolved in 220 ml THF (5% w/v solution) and reprecipitated by slowly adding the polymer solution into 2200 ml of water.

10.1 g of a white copolymer was obtained. As determined by GPC using THF as the solvent, the copolymer has a weight average molecular weight of 178,000 daltons, a number average molecular weight of 84,000 daltons and a polydispersity of 2.1.

Example 5

Poly(DTE co 70% $PEG_{1,000}$ carbonate) is water soluble, so in the final purification step, isopropanol was used instead of water:

1.29 g of DTE (3.60 mmole) and 8.31 g of $PEG_{1,000}$ (8.40 mmole) were placed into a 250 ml flask. Then 50 ml of dry methylene chloride and 3.6 ml of anhydrous pyridine were added. At room temperature, 7.8 ml of a 1.93 M solution of phosgene in toluene was added slowly to the solution with overhead stirring during 90 minutes. 150 ml TBF was added to dilute the reaction mixture. The copolymer was precipitated by slowly adding the mixture into 2000 ml of ethyl ether. The copolymer was redissolved in 70 ml THF (5% w/v solution) and reprecipitated by slowly adding the polymer solution into 700 ml of isopropanol.

6.4 g of a white copolymer was obtained. As determined by GPC using TEF as the solvent, the copolymer has a weight average molecular weight of 47,000 daltons, a number average molecular weight of 37,000 daltons and a polydispersity of 1.3.

Poly(DTB co 1% $PEG_{1,000}$ carbonate), Poly(DTB co 5% $PEG_{1,000}$ carbonate), Poly(DTB co 10% $PEG_{1,000}$ carbonate), Poly(DTH co 1% $PEG_{1,000}$ carbonate), Poly (DTH co 5% $PEG_{1,000}$ carbonate), Poly(DTH co 10% $PEG_{1,000}$ carbonate), Poly(DTH co 20% $PEG_{1,000}$ carbonate) and poly(bisphenol-A co 5% $PEG_{1,000}$ carbonate) were synthesized by similar methods and used for different studies.

Polymer Characterization

Glass Transition Temperature

Copolymers were prepared according to the examples given above. The glass transition temperature ($T_g$) of these copolymers and their corresponding polycarbonate homopolymers were measured (FIG. 1). In each series of copolymers, $T_g$ of the copolymers decreased as the molar fraction of $PEG_{1,000}$ increased.

Mechanical Properties

Tensile modulus: The dry specimens of poly(DTE co 5% $PEG_{1,000}$ carbonate) had tensile modulus of 1.3 Gpa, which is comparable to all tyrosine-derived polycarbonates which have tensile modulus within a range of 1.2–1.6 Gpa. See Ertel et al., *J. Biomed. Mater. Res.*, 28, 919–930 (1994). After 24 h of incubation, the specimens had 10% of water uptake, and the tensile modulus dropped to 0.58 Gpa.

Tensile strength at yield and break: The combination of PEG into the backbone of the tyrosine derived polymer had a profound effect on the tensile strength and ductility of the polymer. While poly(DTE carbonate) was very brittle and failed without yielding after 4% elongation (See the aforementioned Ertel et. al., *J. Biomed. Mater. Res.*, 28, 919–930 (1994)), the poly(DTE co 5% $PEG_{1,000}$ carbonate) did manage to elongate up to 153% before failing. The tensile strength at yield was 41 MPa, at break was 22 MPa. The incubated copolymer became extremely ductile. Film specimens yielded after 6% elongation and failed after up to 650% elongation. The tensile strength at yield was 15 MPa, at break was 19 MPa.

Water Uptake

Figure 2:
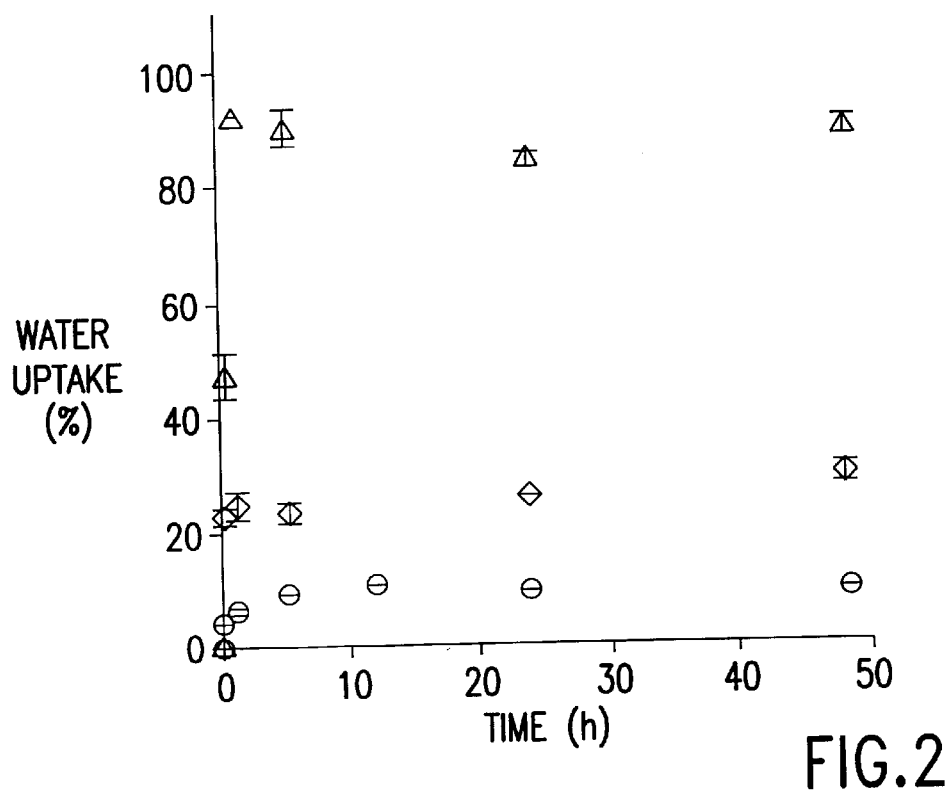
FIG. 2 depicts the water uptake of poly(DTE co 5% $PEG_{1,000}$ carbonate) (○), poly(DTE co 15% $PEG_{1,000}$ carbonate) (◇) and poly(DTE co 30% $PEG_{1,000}$ carbonate) (△) measured as a function of incubation time at 37° C. in phosphate buffered saline.

The amount of water taken up by thin, compression molded films of poly(DTE co $PEG_{1,000}$ carbonates) was determined as described in the experimental section. The compression molded test specimens contained 5 mol %, 15 mol %, or 30 mol % of PEG. Over a 5 h period, poly(DTE co 5% $PEG_{1,000}$ carbonate) reached an equilibrium water uptake of 10%. For poly(DTE co 15%$PEG_{1000}$ carbonate), the equilibrium water uptake after 1 h was 25%. For poly(DTE co 30%$PEG_{1000}$ carbonate) the equilibrium water uptake after only 1 h was 92%. The rate of water uptake and the equilibrium water content increased as the molar fraction of poly(ethylene oxide) increased (FIG. 2). At poly(ethylene oxide) contents above 20%, the copolymers behave increasingly like hydrogels.

Microsphere Formation and Drug Release

The formation of microspheres was studied using poly (DTB co $PEG_{1000}$ carbonates). The homopolymer, poly (DTB carbonate) was included in the studies as control. Next, microspheres were formulated containing either pNA or FITC-dextran. These compounds are useful models for low molecular weight hydrophobic drugs and high molecular weight hydrophilic drugs respectively. As a general rule, microspheres could only be isolated when the PEG content was below 10%. Above that value, microspheres formed initially, but tended to adhere to each other and formed a gum-like precipitate during work up. Thus, free flowing microspheres were formed for the poly(DTB carbonate) and for poly(DTB co 1%$PEG_{1000}$ carbonate) and poly(DTB co 5%$PEG_{1000}$ carbonate). For poly(DTB co 10%$PEG_{1000}$ carbonate), no microspheres could be isolated.

Figure 3:
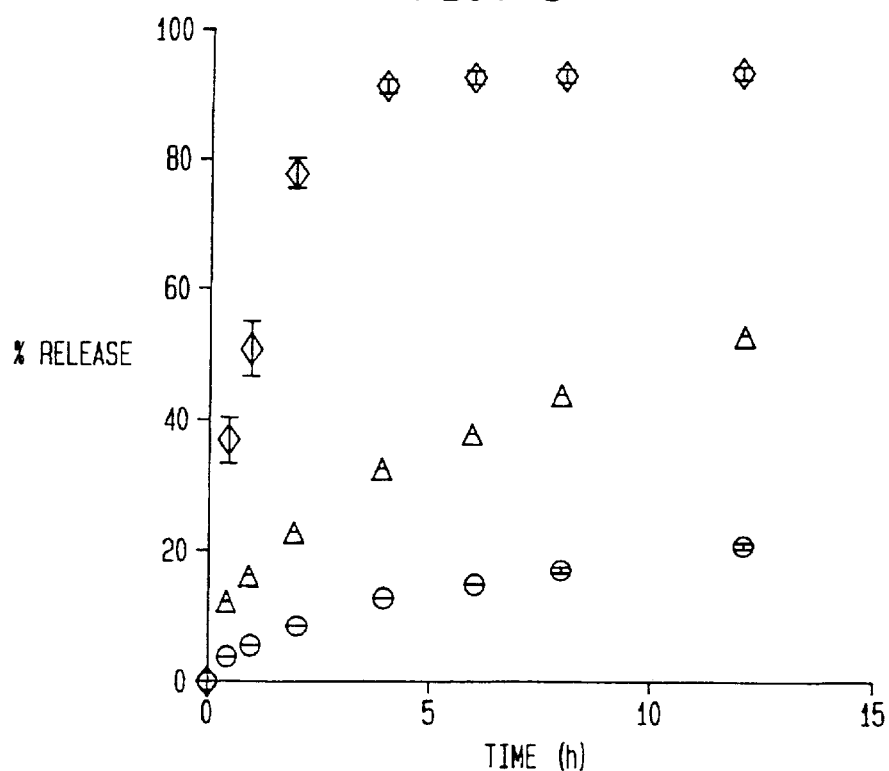
FIG. 3 depicts the pNA release from poly(DTB carbonate) (○), poly(DTB co 1% $PEG_{1,000}$ carbonate) (△) and poly(DTB co 5% $PEG_{1,000}$ carbonate) (◇) microspheres measured as a function of incubation time at 37° C. in phosphate buffer.

It was an unexpected finding that the presence of even very small molar fractions of poly(alkylene oxide) had a significant effect on the drug release rate. This is illustrated in FIG. 3, showing the cumulative release of pNA from the series of copolymers of DTB and $PEG_{1000}$.

Figure 4:
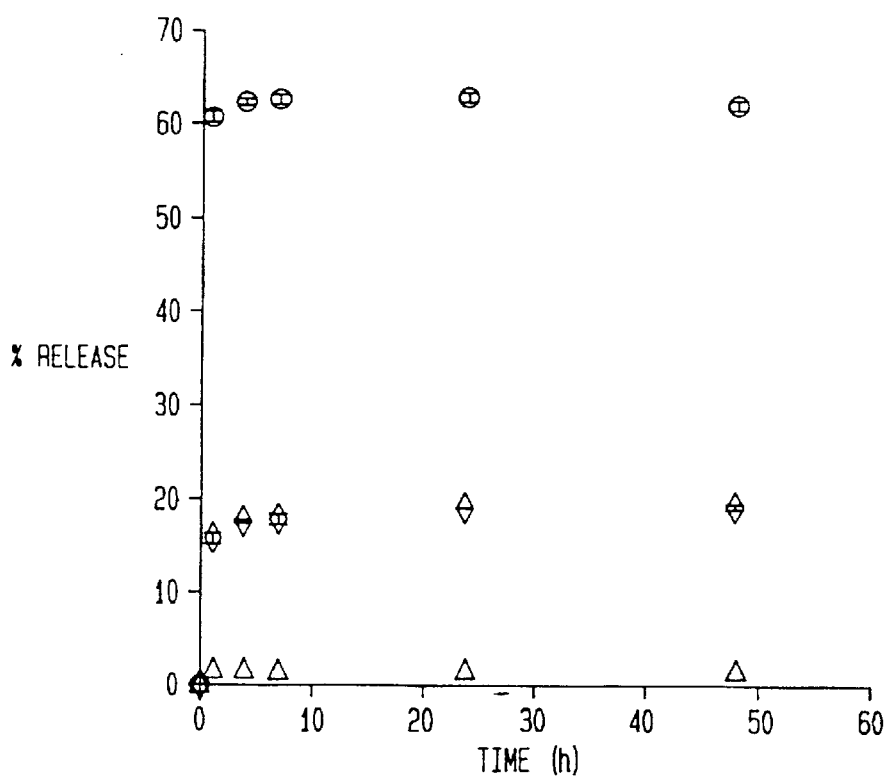
FIG. 4 depicts the FITC-dextran released from microspheres made of poly(DTB carbonate) (△), poly(DTB co 1% $PEG_{1,000}$ carbonate) (◇) and poly(DTB co 5% $PEG_{1,000}$ carbonate) (○) as a function of incubation time at 37° C. in phosphate buffered saline.

The release of FITC-dextran from microspheres made of the homopolymers was extremely slow. The typical release profile for FTIC-dextran from the homopolymers was characterized by a short burst effect followed by a very long lag period during which no further FITC-dextran was released from the microspheres. Including 1 to 5% of $PEG_{1,000}$ in the polymer composition led to a significant increase in the amount of FITC-dextran that was rapidly released from the microspheres (FIG. 4). Thus, the disclosed copolymers can assist in the formulation of controlled drug release systems for hydrophilic, high molecular weight drugs.

Degradation in Vitro

Degradation study was performed for two poly(DTE co $PEG_{1,000}$ carbonates) with poly(bisphenol-A co 5% $PEG_{1,000}$ carbonate) as control. After one day of incubation in buffer at 37° C., thin film specimens of all copolymers had adsorbed water and reached saturation. Contrary to the industrially used very slowly degrading poly(bisphenol-A co PEG carbonates) the tyrosine-derived poly(DTX co PEG carbonates) degraded fast under physiological conditions in vitro, as demonstrated by GPC.

Figure 5:
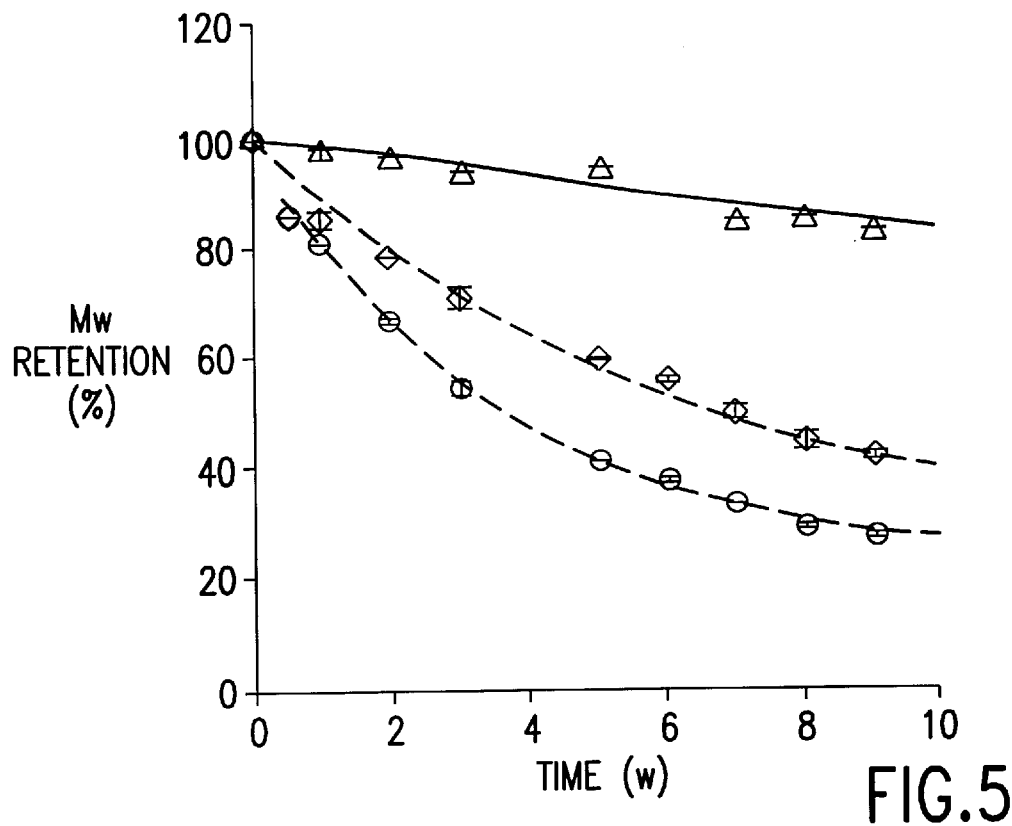
FIG. 5 depicts the molecular weight retention of poly(bisphenol-A co 5% $PEG_{1,000}$ carbonate) (△), poly(DTE co 5% $PEG_{1,000}$ carbonate) (◇) and poly(DTE co 30% $PEG_{1,000}$ carbonate) (○) as a function of incubation time at 37° C. in phosphate buffered saline.

The changes in the molecular weight over time were followed for all three polymers. When the changes were plotted as percent molecular weight retention vs. time, all three polymers had similar degradation profiles, shown for poly(bisphenol-A co 5% $PEG_{1,000}$ carbonate), poly(DTE co 5% $PEG_{1,000}$ carbonate) and poly(DTE co. 30% $PEG_{1,000}$ carbonate) in FIG. 5. During nine weeks of observation, poly(bisphenol-A co 5% $PEG_{1,000}$ carbonate) lost only about 15% of its molecular weight while poly(DTE co 5% $PEG_{1,000}$ carbonate) and poly(DTE co 30% $PEG_{1,000}$ carbonate) lost about 60% and 75% of their molecular weight.

Inverse Temperature Transition

Figure 6:
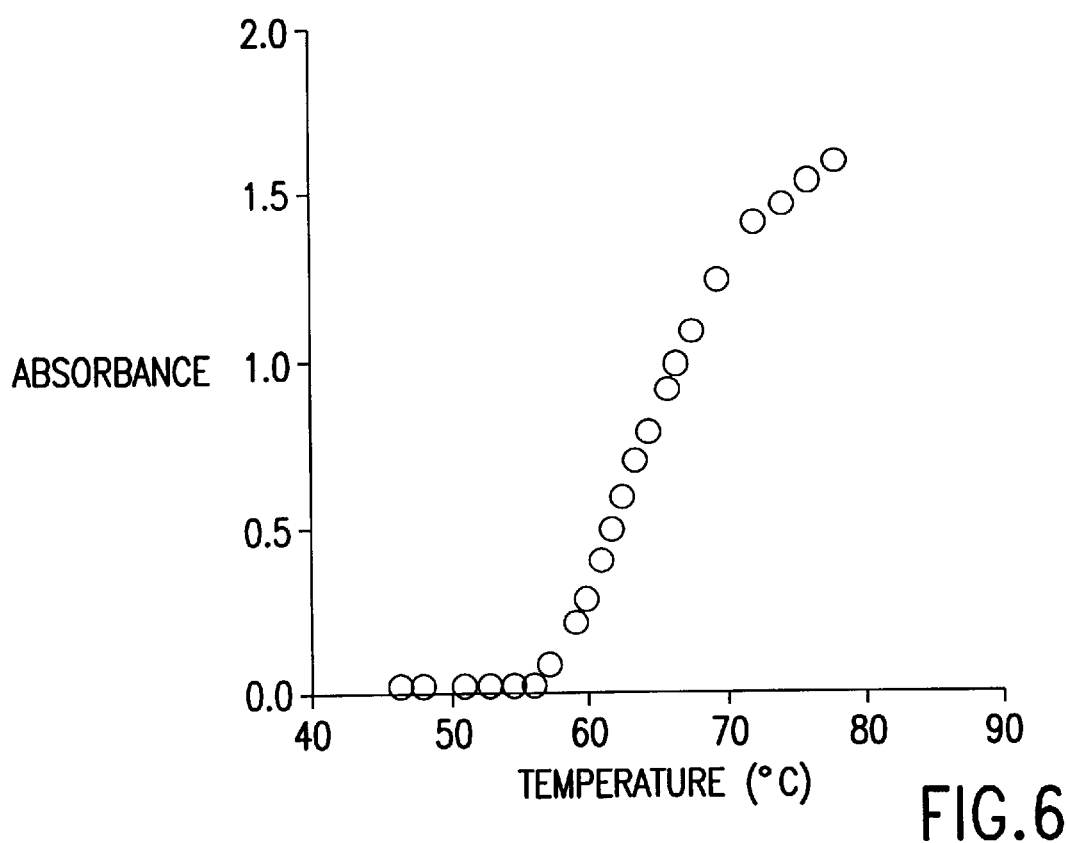
FIG. 6 depicts a turbidity curve for poly(DTE co 70% $PEG_{1,000}$ carbonate) in water at 500 nm.

FIG. 6 illustrates the inverse temperature transition for poly(DTE co 70% $PEG_{1,000}$ carbonate). This polymer is initially in solution as shown by its low absorbence at 500 nm. Upon heating, the polymer precipitates, as indicated by the increasing absorbance. In this particular case, the phase transition starts at 57±1° C.

Cell Growth

The interactions of the polymer with living cells provides important information about possible medical applications. In vitro studies of cell growth also provide an indication of the possible cytotoxicity of a polymer. Such studies are recognized as the first screening tests in the biocompatibility evaluation of medical implant materials according to the FDA Tripartide Biocompatibility guidelines.

Cell growth and spreading decreased as the molar fraction of PEG present in the copolymer increased (Table I). This can be explained by reduced cellular attachment due to the high mobility of the PEG block on the polymer surface. An alternative explanation is based on the general tendency of PEG to prevent the adsorption of proteins onto surfaces. Thus, when PEG is part of the polymer structure, less proteins may be adsorbed to the polymer surface which, in turn, reduces the ability of cells to attach to the surface. It was an unexpected finding that as little as 5% of $PEG_{1,000}$ in the copolymer was sufficient to eliminate almost completely the ability of rat lung fibroblasts cells to attach and grow on the copolymer surfaces. The unattached cells float in the medium and aggregate to each other. Viability tests using trypan blue and calcein AM show that these cells remain viable even after 5 days. This demonstrated that the copolymers are non-cytotoxic.

TABLE I

Cell Attachment And Proliferation On Surfaces Of Copolymers

| PEG Copolymer | | Attachment Proliferation ($\times$ 100 cells/cm$^2$) | |
|---|---|---|---|
| Diphenol | Mole % PEG | 1 day | 5 days |
| DTE | 0 | 46 ± 13 | 596 ± 100 |
|  | 5 | 8 ± 8 | 46 ± 14 |
|  | 15 | 4 ± 5 | 11 ± 10 |
|  | 30 | 3 ± 5 | 11 ± 10 |
| DTB | 0 | 56 ± 17 | 401 ± 79 |
|  | 1 | 50 ± 14 | 163 ± 40 |
|  | 5 | 16 ± 10 | 18 ± 13 |
|  | 10 | 9 ± 9 | 7 ± 7 |
| DTH | 0 | 32 ± 10 | 268 ± 46 |
|  | 1 | 52 ± 31 | 275 ± 71 |
|  | 5 | 9 ± 11 | 3 ± 7 |
|  | 10 | 9 ± 11 | 11 ± 14 |
| Control surfaces |  |  |  |
| glass |  | 50 ± 16 | 555 ± 91 |
| poly (BPA carbonate) |  | 17 ± 10 | 123 ± 37 |

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A method of reducing cellular attachment, migration and proliferation on a polymeric substrate, comprising contacting living cells, tissues or biological fluids containing living cells with a random block copolymer having the formula:

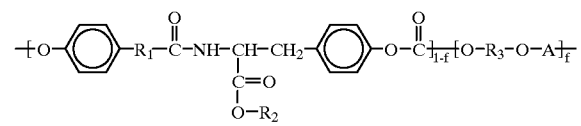

wherein
$R_1$ is —CH=Cl— or (—$CH_2$)$_j$, which j is zero or an integer from one to eight; $R_2$ is selected from the group consisting of straight and branched alkyl and alkylaryl groups containing up to 18 carbon atoms and optionally containing at least one ether linkage, and derivatives of biologically and physiologically active compounds covalently bonded to said copolymer;

each $R_3$ is independently an alkylene group containing up to 4 carbon atoms;

A is selected from the group consisting of:

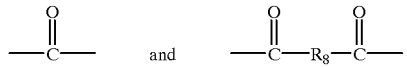

wherein $R_8$ is selected from the group consisting of saturated and unsaturated, substituted and unsubstituted alkyl, aryl and alkylaryl groups containing up to 18 carbon atoms;

y is between about 5 and about 3000; and f is the percent molar fraction of alkylene oxide in said copolymer and ranges between about 1 and about 99 mole percent;

wherein cellular attachment, migration and proliferation decreases as the value of f increases.

2. The method of claim 1, wherein said polymer is in the form of a coating on a medical implant.

3. The method of claim 1, wherein said polymer is in the form of a film.

4. The method of claim 1, wherein said polymer is in the form of a polymeric tissue scaffold.

* * * * *

UNITED STATES PATENT AND TRADEMARK OFFICE
CERTIFICATE OF CORRECTION

PATENT NO. : 6,319,492 B1
DATED : November 20, 2001
INVENTOR(S) : Kohn et al.

It is certified that error appears in the above-identified patent and that said Letters Patent is hereby corrected as shown below:

<u>Column 14,</u>
Line 65, "- CH=Cl -" should read -- -CH=CH- --

Signed and Sealed this

Twenty-first Day of May, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.       : 6,319,492 B1                                     Page 1 of 1
APPLICATION NO.  : 09/520665
DATED            : November 20, 2001
INVENTOR(S)      : Kohn et al.

It is certified that error appears in the above-identified patent and that said Letters Patent is hereby corrected as shown below:

Column 1, line 32, immediately preceding the Background of the Invention section, insert the following ststement:

--GOVERNMENT LICENSE RIGHTS
The U.S. Government may have a paid-up license in this invention and the right in limited circumstances to require the patent owner to license others on reasonable terms as required by the terms of Grant No. GM-49894 awarded by the National Institutes of Health.--

Signed and Sealed this

Twelfth Day of September, 2006

JON W. DUDAS
*Director of the United States Patent and Trademark Office*